United States Patent
Serno et al.

(10) Patent No.: US 6,740,306 B2
(45) Date of Patent: May 25, 2004

(54) IMIDAZOTRIAZINONE-CONTAINING COMPOSITIONS FOR NASAL ADMINISTRATION

(75) Inventors: Peter Serno, Bergisch Gladbach (DE); Andreas Ohm, Neuss (DE); Wolfgang Barth, Shelton, CT (US); Richard-Josef Bauer, Erkrath (DE); Hans-Martin Siefert, Wuppertal (DE); Dieter Zimmer, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/122,694

(22) Filed: Apr. 11, 2002

(65) Prior Publication Data

US 2003/0022894 A1 Jan. 30, 2003

(51) Int. Cl.$^7$ ............ A61K 9/12; A61K 9/14; A61K 31/435
(52) U.S. Cl. ............ 424/45; 424/46; 424/489; 514/248; 514/218; 514/1; 514/221
(58) Field of Search ............ 424/45, 46, 489; 514/248, 218–221

(56) References Cited

U.S. PATENT DOCUMENTS

| | | | |
|---|---|---|---|
| 4,602,099 A | 7/1986 | Parker | 549/479 |
| 6,018,046 A | 1/2000 | Ohashi et al. | 546/62 |
| 6,362,178 B1 | 3/2002 | Niewohner et al. | 514/218 |
| 6,395,736 B1 * | 5/2002 | Parks et al. | 514/248 |

FOREIGN PATENT DOCUMENTS

| | | |
|---|---|---|
| EP | 0463756 | 1/1992 |
| EP | 0967214 | 12/1999 |
| EP | 0992240 | 4/2000 |
| GB | 2315673 | 2/1998 |
| WO | 9428902 | 12/1994 |
| WO | 9632003 | 10/1996 |
| WO | 9703985 | 3/1997 |
| WO | 9915177 | 4/1999 |
| WO | 9924433 | 5/1999 |
| WO | 0000199 | 1/2000 |

OTHER PUBLICATIONS

Lacy et al, Drug Infromation handbook, 1993, by Lexi-comp, pp. 511–513.*

XP–001119414, Sommer, F., Engelmann, U., "Vardenafil Bayer Yakuhin", Curr. Opin. In Invest. Drugs, 3 (4): 607–613 (2002).

Murray, K., "Phosphodiesterase $V_A$ Inhibitors", DN&P, 6: 150–156 (Apr. 1993).

Rajfer, J., Aronson, W., Bush, P., Dorey, F., Ignarro, L., "Nitric Oxide as a Mediator of Relaxation of the Corpus Cavernosum in Response to Nonadrenergic, Noncholinergic Neurotransmission", New England J. of Med., 326: 90–94 (Jan. 1992).

* cited by examiner

Primary Examiner—Thurman K. Page
Assistant Examiner—Mina Haghighatian
(74) Attorney, Agent, or Firm—Susan M. Pellegrino

(57) ABSTRACT

The present invention relates to imidazotriazinone-containing compositions for nasal administration which, besides the cGMP PDE inhibitor, contain a small amount of a local anaesthetic.

31 Claims, No Drawings

IMIDAZOTRIAZINONE-CONTAINING COMPOSITIONS FOR NASAL ADMINISTRATION

The present invention relates to imidazotriazinone-containing compositions for nasal administration which, besides the imidazotriazinone, contain a small amount of a local anaesthetic.

Cyclic guanosine-3',5'-monophosphate phosphodiesterase inhibitors, abbreviated to cGMP PDE inhibitors, have a well known range of effects (cf., for example, EP-A-0 463 756, WO 99/24433). The imidazotriazinones encompassed by the present invention are described in WO 99/24433 as such cGMP PDE inhibitors. Inter alia, the biochemical bases of the process of penile erection were elucidated a few years ago and, on this basis, it was reported that cGMP PDE inhibitors, in particular PDE5 inhibitors, are suitable for treating male erectile dysfunction (cf. Rajfer et al., New England J. Med. 326 (1992), 90; Murray, Drug News & Perspectives 6 (1993), 150). Subsequently, the use of certain cGMP PDE inhibitors for treating male erectile dysfunction was described in WO 94/28902, and one of these (sildenafil citrate, Viagra®) is now proved as medicament which can be administered orally for this indication. One disadvantage of oral administration is, however, that the onset of action is delayed, which is deleterious to the spontaneity desired by the patient especially in this indication. In addition, first pass effects or food effects may impair the efficacy of an orally administered medicament.

In principle, it ought to be possible by nasal administration of an active ingredient to achieve a faster rise in the level of active ingredient in the blood stream and, associated therewith, an accelerated onset of action. There has thus been no lack of proposals in the prior art that cGMP PDE inhibitors be administered nasally, especially for treating male erectile dysfunction (cf. WO 96/32003, WO 97/03985, WO 98/53819, WO 99/24433, EP-A-0 967 214, WO 00/00199). For example, EP-A-0 967 214 describes nasal administration of a sildenafil salt which has better solubility in water, namely sildenafil mesylate, and the faster rise in the level of active ingredient in the blood stream which can be achieved thereby with a smaller amount of active ingredient being necessary compared with the oral route.

However, problems may arise on nasal administration of cGMP PDE inhibitors. Owing to their mechanism of action, these substances are vasodilators. Since PDE5 also occurs in the tissue of the nasal cavity, nasal administration of PDE 5 inhibitors leads to local dilation of the vessels of the nasal mucosa. The result is a condition in the nose which the patient finds unpleasant, such as itching or stinging, or eye-watering, an increase in the nasal airway resistance and/or a nasal blockage, although no local irritation is detectable toxicologically. Although it was described in EP-A-0 967 214 that these effects do not impair rapid absorption of sildenafil mesylate, the unpleasant condition in the nose, which is found to be upsetting particularly during sexual intercourse, the increase in the nasal airway resistance or the nasal blockage remain a not inconsiderable disadvantage.

EP-A-0 992 240, which corresponds to WO 98/53819, proposes to avoid an inadequate absorption of the cGMP PDE inhibitor, caused by the abovementioned disadvantages, by adding vasoconstricting active ingredients such as epinephrine, naphazoline nitrate, tramazoline hydrochloride or tetrazoline, antiallergic substances such as sodium cromoglicate or ketotifen fumarate, suppressors of nasal mucosal secretion such as flutropium bromide or steroids such as, for example, prednisolone, without showing by way of example that this sufficiently prevents the occurrence of the unpleasant feeling for the patient which has been described above.

Nasal administration of local anaesthetics has to date been disclosed for surface anaesthesia before surgical operations in the nasal region. In addition, U.S. Pat. No. 4,602,099 has described the use of local anaesthetics as adjuvants in antirhinoviral medicaments for additional treatments of the symptoms of a rhinovirus infection. The only example of a local anaesthetic used in this patent was benzyl alcohol. It should be noted that benzyl alcohol is also known as preservative or as solubilizer and is described in these functions in EP-A-0 967 214 and WO 00/00199 as one of a plurality of adjuvants which can be used additionally for the formulations mentioned therein. In addition, it has emerged within the scope of the present invention that benzyl alcohol is unable to reduce or prevent the disadvantages described above which occur on nasal administration of cGMP PDE-inhibitors.

WO 99/15171 describes liquid crystal nicotine preparations to which a local anaesthetic is added to avoid disadvantageous effects of nicotine caused by its local irritant effect. In this case, the local anaesthetic acts by blocking peripheral pain receptors. It should be noted that cGMP PDE inhibitors on nasal administration cause such a local irritant effect to only a small extent or not at all.

GB-A-2 315 673 proposed intranasal administration of local anaesthetics such as lidocaine in addition to a 5-HT1D agonist for the treatment of migraines. Besides the effect of interrupting pain transmission which is known for local anaesthetics, this proposal is based on the vasodilating effect of local anaesthetics, which leads to an accelerated absorption of the 5-HT1D agonist and thus to a faster onset of action.

It would therefore have been expected that the disadvantages, described above, based on the vasodilating properties of cGMP PDE inhibitors would be further enhanced through the presence of a local anaesthetic because of its vasodilating effect.

It was the object of the present invention to find an imidazotriazinone-containing composition for nasal administration whose use is not associated with disadvantages such as a nasal condition which is found to be unpleasant, eye-watering, an increase in the nasal airway resistance or nasal blockage.

The above object is achieved by a composition which comprises at least one imidazotriazinone and at least one local anaesthetic, the local anaesthetic not being benzyl alcohol.

It has been found, surprisingly, that only a small amount of a local anaesthetic needs to be added to the imidazotriazinone-containing compositions, to overcome the disadvantages described above. The doses of local anaesthetic necessary for this purpose are generally distinctly less than those necessary for surface anaesthesia. A feeling of local numbness, as occurs after blockade of nerves conducting irritation, by, for example, a local anaesthetic, can therefore be avoided on use of the compositions according to the invention. Furthermore, addition of local anaesthetics to nasal compositions of the cGMP PDE inhibitors according to the invention surprisingly does not lead to build-up of excessive peaks in the plasma levels as would have been expected on the basis of the vasodilating properties of local anaesthetics and the accelerated and increased absorption of the cGMP PDE inhibitor in the nose which was thus to be expected. Thus, on use of the compositions according to the invention, no disadvantages in relation to the duration of action or increased side effects occur.

According to the present invention, the cGMP PDE inhibitor contained in the compositions is a compound of the formula (I)

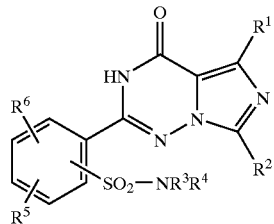

in which
- $R^1$ represents hydrogen or straight-chain or branched alkyl having up to 4 carbon atoms,
- $R^2$ represents straight-chain alkyl having up to 4 carbon atoms,
- $R^3$ and $R^4$ are identical or different and represent a straight-chain or branched alkyl chain having up to 5 carbon atoms, which is optionally substituted up to twice, identically or differently, by hydroxyl or methoxy, or
- $R^3$ and $R^4$ form, together with the nitrogen atom, a piperidinyl, morpholinyl, thiomorpholinyl ring or a radical of the formula

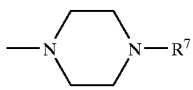

in which
- $R^7$ denotes hydrogen, formyl, straight-chain or branched acyl or alkoxycarbonyl having in each case up to 6 carbon atoms, or denotes straight-chain or branched alkyl having up to 6 carbon atoms which is optionally substituted once to twice, identically or differently, by hydroxyl, carboxyl, straight-chain or branched alkoxy or alkoxycarbonyl having in each case up to 6 carbon atoms, or denotes $C_{3-8}$-cycloalkyl, and the heterocycles mentioned under $R^3$ and $R^4$, which are formed together with the nitrogen atom, are optionally substituted once to twice, identically or differently, optionally also geminally, by hydroxyl, formyl, carboxyl, straight-chain or branched acyl or alkoxycarbonyl having in each case up to 6 carbon atoms,
and/or the heterocycles mentioned under $R^3$ and $R^4$, which are formed together with the nitrogen atom, are optionally substituted by straight-chain or branched alkyl having up to 6 carbon atoms, which is optionally substituted once to twice, identically or differently, by hydroxyl or carboxyl,
and/or the heterocycles mentioned under $R^3$ and $R^4$, which are formed together with the nitrogen atom, are optionally substituted by N-linked piperidinyl or pyrrolidinyl,
- $R^5$ and $R^6$ are identical or different and represent hydrogen, straight-chain or branched alkyl having up to 6 carbon atoms, hydroxyl or represent straight-chain or branched alkoxy having up to 6 carbon atoms, and salts, isomers and/or hydrates thereof.

Compositions particularly preferred according to the invention contain as cGMP PDE inhibitor 2-{2-ethoxy-5-[(4-ethylpiperazin-1-yl)sulphonyl]phenyl}-5-methyl-7-propylimidazo[5,1-f][1,2,4]triazin-4(3H)-one (vardenafil), or its pharmaceutically acceptable salts, isomers and/or hydrates such as the corresponding hydrochloride, hydrochloride trihydrate, citrate or mesylate.

The compounds of the formula (I) can, for example, be prepared as described in WO 99/24433.

Unless otherwise indicated, the substituents generally have the following meaning for the purpose of the present invention:

Alkyl generally represents a straight-chain or branched hydrocarbon radical having 1 to 6 carbon atoms. Examples which may be mentioned are methyl, ethyl, propyl, isopropyl, butyl, isobutyl, pentyl, isopentyl, hexyl, isohexyl.

Acyl generally represents straight-chain or branched lower alkyl having 1 to 6 carbon atoms which is linked via a carbonyl group. Examples which may be mentioned are: acetyl, ethylcarbonyl, propylcarbonyl, isopropylcarbonyl, butylcarbonyl and isobutylcarbonyl.

Alkoxy generally represents a straight-chain or branched hydrocarbon radical having 1 to 6 carbon atoms which is linked via an oxygen atom. Examples which may be mentioned are methoxy, ethoxy, propoxy, isopropoxy, butoxy, isobutoxy, pentoxy, isopentoxy, hexoxy, isohexoxy. The terms "alkoxy" and "alkyloxy" are used synonymously.

Alkoxycarbonyl can be represented, for example, by the formula

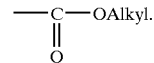

Alkyl in this case generally represents a straight-chain or branched hydrocarbon radical having 1 to 6 carbon atoms. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

Cycloalkyl generally represents a cyclic hydrocarbon radical having 3 to 8 carbon atoms. Cyclopropyl, cyclopentyl and cyclohexyl are preferred. Examples which may be mentioned are cyclopentyl, cyclohexyl, cycloheptyl and cyclooctyl.

Heterocycle generally represents for the purpose of the invention a saturated, unsaturated or aromatic 3- to 6-membered, for example 5- or 6-membered, heterocycle which may contain up to 3 heteroatoms from the series S, N and/or O and, in the case of a nitrogen atom, may also be linked via the latter. Examples which may be mentioned are: oxadiazolyl, thiadiazolyl, pyrazolyl, pyridyl, pyrimidinyl, pyridazinyl, pyrazinyl, thienyl, furyl, pyrrolyl, pyrrolidinyl, piperazinyl, tetrahydropyranyl, tetrahydrofuranyl, 1,2,3-triazolyl, thiazolyl, oxazolyl, imidazolyl, morpholinyl or piperidyl. Thiazolyl, furyl, oxazolyl, pyrazolyl, triazolyl, pyridyl, pyrimidinyl, pyridazinyl and tetrahydropyranyl are preferred. The term "heteroaryl" (or "hetaryl") represents an aromatic heterocyclic radical.

The above compounds of the formula (I) may also be present in the form of their salts. Mention may be made here in general of salts with organic or inorganic bases or acids.

Physiologically acceptable salts are preferred for the purpose of the present invention. Physiologically acceptable salts of the compounds according to the invention may be salts of the substances according to the invention with mineral acids, carboxylic acids or sulphonic acids. Particularly preferred examples are salts with hydrochloric acid, hydrobromic acid, sulphuric acid, phosphoric acid, methanesulphonic acid, ethanesulphonic acid, p-toluenesulphonic acid, benzenesulphonic acid, naphthalinedisulphonic acid, acetic acid, propionic acid, lactic acid, tartaric acid, citric acid, fumaric acid, maleic acid or benzoic acid, and sugar acids such as glucuronic acid or lactobionic acid.

Physiologically acceptable salts may likewise be metal or ammonium salts of the compounds according to the invention which have a free carboxyl group. Particularly preferred examples are sodium, potassium, magnesium or calcium salts, and ammonium salts which are derived from ammonia or organic amines such as, for example, ethylamine, di- or triethylamine, di- or triethanolamine, dicyclohexylamine, dimethylaminoethanol, arginine, lysine or ethylenediamine.

The compounds of the formula (I) may exist in isomeric forms. This means according to the present invention stereoisomeric forms which either are related as image and mirror image (enantiomers) or nonrelated as image and mirror image (diastereomers). The invention relates both to the enantiomers or diastereomers and to mixtures thereof in each case. The racemic forms may, just like the diastereomers, be separated in a known manner, for example by racemate resolution or chromatographic separation, into the stereoisomerically pure constituents. Double bonds present in the compounds according to the invention may be in the cis or trans configuration (Z or E form).

The compounds of the formula (I) may also exist in the form of hydrates, in which case both hydrates of the free compounds and hydrates of salts thereof are encompassed by the present invention. One example of a hydrate of a salt is vardenafil hydrochloride trihydrate.

Compared with the amounts of cGMP PDE inhibitor required for oral administration, preferably amounts of only from 0.001 mg/kg to 0.5 mg/kg of cGMP PDE inhibitor are necessary with the compositions according to the invention which are to be administered nasally.

The local anaesthetics which can be used according to the invention are known per se and are listed, for example, in Remington's Pharmaceutical Sciences 1990, pp. 1048–1056. Local anaesthetics are compounds which reversibly inhibit the excitability of sensory nerve endings or the neuronal conductivity for pain or other sensory stimuli in a limited region of the body without causing permanent harm (cf. J. L. McGuire (editor), Pharmaceuticals, volume 2, Wiley-VCH, Weinheim 2000, pp. 539 et seq., Helwig/Otto, Arzneimittel [Medicinal products], volume II, Wissenschaftliche Verlagsgesellschaft mbH Stuttgart, 2000, pp. 37-1 et seq.). Local anaesthetics within the meaning of the present invention are preferably intended to mean substances which are listed in the Index Nominum 2000, International Drug Directory, Scientific Publishers Stuttgart 2000 with the therapeutic category "local anaesthetic". Express reference is hereby made to the content concerning this in this reference.

Local anaesthetics preferred according to the present invention are compounds of the formula (II)

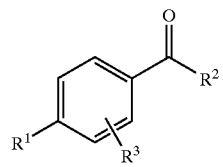

(II)

in which $R^1$ represents H, $NH_2$, $NH(C_{1-6}$-alkyl), $O—C_{1-6}$-alkyl or $CH_2OPh$;

$R^2$ represents $O-C_{1-6}$-alkyl which may optionally have a radical from the group consisting of $NH(C_{1-6}$-alkyl), $N(C_{1-6}$-alkyl$)_2$ or a saturated 5- or six-membered heterocycle which contains at least one nitrogen atom and is linked via the latter, and optionally one or two further heteroatoms from the group consisting of N, O, S, and optionally carries one to three further $C_{1-6}$-alkyl radicals, or represents $(CH_2)_{1-6}$-Het, where Het represents a saturated 5- or six-membered heterocycle which contains at least one nitrogen atom and is linked via the latter, and optionally one or two further heteroatoms from the group consisting of N, O, S, and optionally carries one to three further $C_{1-6}$-alkyl radicals;

$R^3$ represents H, halogen or $O—C_{1-6}$-alkyl;

or compounds of the formula (III)

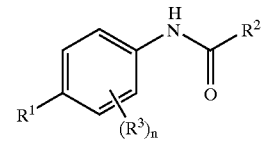

(III)

in which $R^1$ represents H or OH;

$R^2$ represents $C_{1-6}$-alkyl-$N(C_{1-6}$-alkyl$)_2$ where the bridging alkyl chain may optionally carry one or more $C_{1-6}$-alkyl radicals, or represents a saturated 5- or six-membered heterocycle which contains at least one nitrogen atom and optionally one or two further heteroatoms from the group consisting of N, O, S, and optionally carries one to three further $C_{1-6}$-alkyl radicals, $R^3$ represents $C_{1-6}$-alkyl, halogen or $COOC_{1-6}$-alkyl;

n represents 1 or 2;

or a compound from the group consisting of

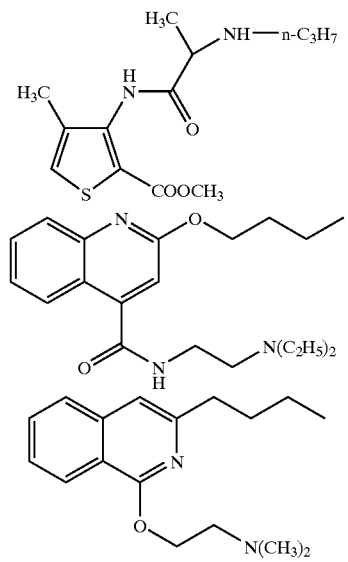

-continued

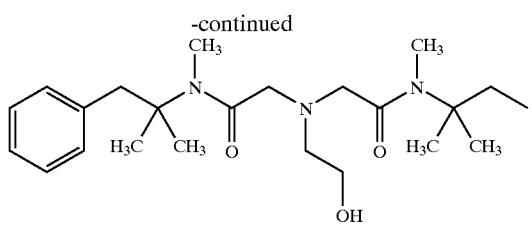

and polidocanol and benoxinate, and physiologically acceptable salts and/or hydrates thereof.

Particularly preferred local anaesthetics according to the invention are those of the formula (II)
in which
$R^1$ represents H, $NH_2$, NH-n-$C_4H_9$, O-n-$C_3H_7$, O-n-$C_4H_9$ or $CH_2OPh$;
$R^2$ represents $OC_2H_5$, O-n-$C_4H_9$, O—$(CH_2)_2N(C_2H_5)_2$, $O(CH_2)_2$, or a radical from the group consisting of

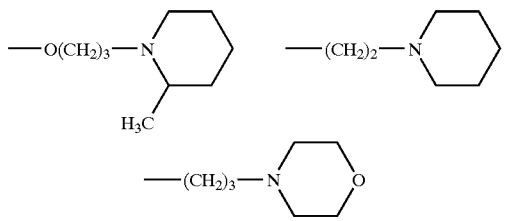

$R^3$ represents H, Cl, O-n-$C_3H_7$ or O-n-$C_4H_9$;
or compounds of the formula (III)
in which
$R^1$ represents H or OH;
$R^2$ represents $CH_2N(C_2H_5)_2$, $CHCH_3NH$-n-$C_3H_7$, $CH_2NH$-n-$C_4H_9$ or a radical from the group consisting of

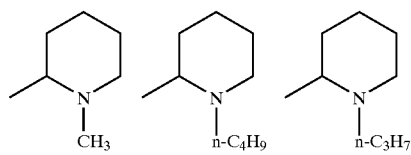

$R^3$ represents $CH_3$, Cl or $COOCH_3$;
n represents 1 or 2;
and benoxinate and physiologically acceptable salts and/or hydrates thereof.

The local anaesthetics which can be particularly preferably employed according to the invention are: benzocaine, butambene, piperocaine, piperocaine hydrochloride, procaine, procaine hydrochloride, chloroprocaine, chloroprocaine hydrochloride, oxybuprocaine, oxybuprocaine hydrochloride, proxymetacaine, proxymetacaine hydrochloride, tetracaine, tetracaine hydrochloride, nirvanin, lidocaine, lidocaine hydrochloride, prilocaine, prilocaine hydrochloride, mepivacaine, mepivacaine hydrochloride, bupivacaine, bupivacaine hydrochloride, ropivacaine, ropivacaine hydrochloride, etidocaine, etidocaine hydrochloride, butanilicaine, butanilicaine hydrochloride, articaine, articaine hydrochloride, cinchocaine, cinchocaine hydrochloride, oxetacaine, oxetacaine hydrochloride, propipocaine, propipocaine hydrochloride, dyclonine, dyclonine hydrochloride, pramocaine, pramocaine hydrochloride, fomocaine, fomocaine hydrochloride, quinisocaine, quinisocaine hydrochloride, benoxinate and polidocanol. These compounds are commercially available or can be prepared in a way known to the skilled person, for example as described in J. L. McGuire (editors), Pharmaceuticals, volume 2, Wiley-VCH 2000, pp. 539 et seq.

Local anaesthetics which can preferably be used according to the invention are benzocaine, lidocaine, tetracaine, benoxinate, polidocanol or their pharmaceutically acceptable salts. Lidocaine hydrochloride and lidocaine methanesulphonate are particularly preferred according to the invention.

However, it should be pointed out once again that benzyl alcohol, which is occasionally referred to as a local anaesthetic, is not encompassed by the present invention because it proved to be unsuitable for overcoming the disadvantages described above and, in addition, led to local irritation of the nasal mucosa.

The compositions according to the invention contain the local anaesthetic(s) in lower concentrations than the standard amount in commercially available topical preparations for surface anaesthesia, namely in a concentration of less than 4% (m/v), preferably less than 3% (m/v), where % (m/v) represents % mass/volume, that is to say 3% (m/v) means, for example, 3 g of substance in 100 ml of solution. According to the present invention, lidocaine is present in the compositions according to the invention in a concentration of less than 4% (m/v), preferably from 0.5 to 3.0% (m/v), which, with an administered volume of 100 µl, corresponds to a single dose of less than 4 mg, preferably 0.5–3 mg. This is below the concentration of lidocaine in the commercial product Xylocain® 4%, which contains, for surface anaesthesia in the ear, nose and throat sector, 200 mg of lidocaine per 5 ml of volume (Rote Liste 1999, Editio Cantor, Aulendorf). According to the present invention, oxybuprocaine (benoxinate) is present in the compositions according to the invention in a concentration of less than 1% (m/v) (corresponding to a single dose of 0.5 mg/50 µl), preferably of 0.1–0.8% (m/v). For comparison, during surface anaesthesia in rhinology, a single dose of up to 105 mg of benoxinate per 70 kg of body weight is recommended (specialist information service Novesine® Wander 1%, 1998, quoted in: Drugdex Drug Evaluations, Micromedex 2001, Engelwood, Colo., USA). According to the present invention, tetracaine is present in the compositions according to the invention in a concentration of less than 0.5 mg per single dose, preferably of less than 0.25 mg per single dose. For comparison, up to 20 mg of tetracaine is recommended for mucosal anaesthesia of the nose (Reynolds 1990, quoted in: Drugdex Drug Evaluations, Micromedex 2001, Engelwood, Colo., USA).

Intranasal preparations are known from the state of the art. The compositions according to the invention can be formulated analogously as solution, suspension, emulsion or powder for atomization in order to be sprayed, aspirated or introduced dropwise into the nose or applied to the mucous wall of the nose. Formulations in the form of a solution, suspension, for example a nanoparticle suspension, or emulsion can be administered as drop preparation for example from a nose drop bottle or a pipette, pump spray pack or compressed gas pack (for example an aerosol or an atomizing device), which can be calibrated in such a way that delivery of a fixed amount of the active ingredient(s) is possible. Powder preparations can be sprayed into the nose for example from a capsule provided with small perforations by means of a stream of air generated for example by a rubber bulb. All the preparation forms may represent multidose containers or divided single-dose containers.

Commercially available nasal applicators are, for example, the Pfeiffer unit dose and bidose system, the Valois monospray, bidose and monopowder system or the Becton-Dickinson Accuspray® system. Also suitable are glass or plastic bottles with commercially available metering pump spray heads.

Nanoparticle suspensions can be obtained by grinding powdered ingredients of the compositions according to the invention or by finely divided precipitation from solutions of ingredients of the formulations according to the invention and usually display improved solubility properties.

The compositions according to the invention contain, when formulated in liquid form, solvents and, where appropriate, one or more excipients such as, for example, buffers or substances for adjusting pH, viscosity-increasing substances, preservatives, surfactants, solubilizers, tonicity agents, antioxidants and/or flavourings.

Solvents which can be used according to the invention are water, glycerol, polyethylene glycol, propylene glycol or medium-chain triglycerides.

It is preferred according to the invention for liquid formulations of the compositions according to the invention to be adjusted to a pH in the range from 2 to 9, preferably 3 to 8, in order to avoid irritation in the nose and optimize the absorption of the cGMP PDE inhibitors. According to the present invention, this can be achieved by adding lactic acid (lactate), acetate, phosphate or citrate buffers or by adding methanesulphonic acid, hydrochloric acid, sulphuric acid, toluenesulphonic acid, gluconic acid, glucuronic acid, lactobionic acid, nitric acid, sodium hydroxide, potassium hydroxide, sodium carbonate or trometamol.

Viscosity-increasing excipients are, for example, polymers such as hydroxypropylmethylcellulose, hydroxypropylcellulose, methylcellulose, hydroxyethylcellulose, carboxymethylcellulose, carbomer, polyvinylpyrrolidone, polyvinyl alcohol or xanthan gum. Sugars or sugar alcohols such as sorbitol can also be used according to the present invention. The concentration of viscosity-increasing excipients in the compositions according to the invention can be chosen depending on the substance used and the required viscosity of the composition according to the invention.

The compositions according to the invention may furthermore contain one or more preservatives such as, for example, benzalkonium chloride, sorbic acid or its salts or benzoic acids or its salts, parabens such as methylparaben or propylparaben, chlorobutanol or thiomersal. The concentration of the preservative in the compositions according to the invention can be chosen depending on the substance used and the required application. A preservative if used is typically present in the compositions according to the invention in a concentration of up to 2% (m/v).

According to the present invention, the compositions according to the invention may also contain one or more surfactants and/or solubilizers in order, where appropriate, to increase the solubility of the cGMP PDE inhibitor used. It is possible to use for example according to the present invention polysorbates, polyethylene glycol, polyoxyethylene derivatives of fatty acid monoesters of sorbitol anhydrides such as, for example, Tween 80, polyoxyl 40 stearate, polyoxyethylene 50 stearate, bile salts, octoxynol, polyoxyethylated castor oil, polyoxystearate, poloxamers, phospholipid, benzoic acid, caffeine, vanillin, urea, nicotinamide, cyclodextrins or cyclodextrin ethers. It is possible according to the invention to use nonionic, anionic or cationic additives of the above categories. The concentration of the surfactants and/or solubilizers in the compositions according to the invention can be chosen depending on the substance used and the desired application. A surfactant and/or solubilizer if used is typically present in the compositions according to the invention in a concentration of from 0.001% (m/v) to about 5% (m/v).

According to the present invention, the compositions according to the invention may also contain one or more tonicity agents. Examples which can be used for this purpose according to the present invention are sodium chloride, calcium chloride, glycerol, mannitol or glucose. The concentration of the tonicity agents in the compositions according to the invention can be chosen depending on the substance used and the desired application. A tonicity agent if used is typically present in the compositions according to the invention in a concentration of from 0.001% (m/v) to about 5% (m/v).

According to the present invention, the compositions according to the invention may also contain one or more antioxidants. Examples which can be used for this purpose according to the present invention are sodium metabisulphite, sodium bisulphite, ascorbic acid and its salts, butylated hydroxytoluene, butylated hydroxyanisole, metal chelators such as ethylenediaminetetraacetic acid, propyl gallate, ascorbyl palmitate or tocopherol. The concentration of the antioxidants in the compositions according to the invention can be chosen depending on the substance used and the desired application. An antioxidant if used is typically present in the compositions according to the invention in a concentration of from 0.001% (m/v) to about 5% (m/v).

According to the present invention, the compositions according to the invention may also contain one or more flavourings. Examples which can be used for this purpose according to the present invention are saccharin sodium, aspartame, acesulphame potassium or menthol. The concentration of the flavourings in the compositions according to the invention can be chosen depending on the substance used and the desired application. A flavouring if used is typically present in the compositions according to the invention in a concentration of from 0.001% (m/v) to about 5% (m/v).

If the compositions according to the invention are administered in the from of compressed gas packs, these compressed gas packs additionally contain propellant gases such as, for example, propane, butane, nitrogen or nitrous oxide.

According to the present invention, compositions according to the invention in powder form additionally contain carriers such as, for example, glucose, sucrose, mannitol, crystalline cellulose or lactose.

According to the present invention, compositions according to the invention in powder form may also contain substances to prolong the contact time with the nasal mucosa such as, for example, polymers such as carbomer, chitosan or cellulose ethers. The concentration of these excipients in the compositions according to the invention can be chosen depending on the substance used and the desired application. Such an excipient is if used typically present in the compositions according to the invention in a concentration of from 0.001% (m/v) to about 5% (m/v).

According to the present invention, compositions according to the invention may additionally contain humectants in order to prevent or reduce drying out of the mucous membrane and thus prevent irritation. Examples which can be used for this purpose according to the present invention are sorbitol, propylene glycol or glycerol. The concentration of the humectant in the compositions according to the invention can be chosen depending on the substance used and the desired application. A humectant is if used typically present in the compositions according to the invention in a concentration of from 0.001% (m/v) to about 5% (m/v).

The present invention is described in detail below by means of non-restrictive preferred examples. Unless otherwise indicated, all quantitative data relate to percentages by weight.

EXAMPLES

Soluble formulations can be produced in a simple manner by dissolving the ingredients in the chosen solvent, then filtering the solution, charging the intended containers under aseptic conditions and, where appropriate, sterilizing with heat.

The cGMP PDE inhibitor can in this case be employed in the form of its salt chosen for a formulation. Alternatively, the free base can be added together with an appropriate acid to the above solution so that the corresponding salt is formed only in the solution. The subsequent further processing takes place in analogy to the procedure described above. It is thus possible for example to add the cGMP PDE inhibitor vardenafil in the form of its hydrochloride trihydrate or as free base together with hydrochloric acid to the above solution.

For administering higher doses and for avoiding stability problems, it may be advantageous to formulate the compositions according to the invention as powders. In this case, a particle size distribution of the powder formulation in the range from 1 to 100 μm, preferably from 5 to 40 μm, is desired because smaller particles may pass through the nose into the lungs, whereas larger particles are to some extent inadequately absorbed.

The appropriate containers for the finished formulations are known to the skilled person and are conventionally used single-dose or multidose containers.

Purified water means purified water as defined in the European Pharmacopoeia (Ph. Eur.) which is known to the skilled person. This is demineralized water of standardized quality.

Example 1

A solution was prepared from the following ingredients:

| | |
|---|---|
| Vardenafil hydrochloride trihydrate | 1.778 g |
| Benoxinate HCl | 0.500 g |
| Lactic acid 20% | 0.805 g |
| Glycerol anhydrous | 2.100 g |
| Purified water | 95.657 g |
| | 100.840 g = 100 ml |

The solution was then sterilized by filtration and packed into single-dose nasal applicators. 67 μl of this solution contain 1 mg of the cGMP PDE inhibitor employed.

Comparative Example 1

A solution was prepared in analogy to Example 1 but the benoxinate HCl was replaced by purified water.

Example 2

A solution was prepared from the following ingredients:

| | |
|---|---|
| Vardenafil | 2.000 g |
| Lidocaine | 1.000 g |
| Methanesulphonic acid | 0.902–1.000 g (ad pH 3.7) |
| Glycerol anhydrous | 2.000 g |
| Purified water | 95.168–95.070 g |
| | 101.07 g |

100 μl of this solution were introduced together with an excess of 20% into the product container of a single-dose nasal spray applicator and heat sterilized at a temperature of more than 121° C. for 15 minutes. The product container was then incorporated into a single-dose nasal spray applicator. After actuation of the applicator in each case 100 μl of solution (which corresponds to 2 mg of the cGMP PDE inhibitor employed) are delivered as aerosol.

Example 3

A solution was prepared from the following ingredients:

| | |
|---|---|
| Vardenafil | 2.00 g |
| Lidocaine | 1.00 g |
| Methanesulphonic acid[1]) | 0.902–1.000 g |
| Glycerol anhydrous | 1.20 g |
| Hypromellose | 2.00 g |
| Purified water | 94.418–94.320 g |
| | 101.52 g |

[1])ad pH 3.7

The ingredients are dissolved in water, filtered, introduced in 120 μl portions into plastic tubes and heat sterilized. It is possible to remove from each tube 100 μl of solution corresponding to a single dose of 2 mg of the cGMP PDE inhibitor employed and administer it nasally.

Comparative Example 2

A solution was prepared in analogy to Example 3 but lidocaine and the amount of methanesulphonic acid needed to form a salt with lidocaine were omitted:

| | |
|---|---|
| Vardenafil | 2.00 g |
| Methanesulphonic acid[1]) | 0.492–0.590 g |
| Glycerol anhydrous | 2.00 g |
| Hypromellose | 2.00 g |
| Purified water | 94.988–94.89 g |
| | 101.48 g |

[1])ad pH 3.7

Example 4

A solution was prepared from the following ingredients:

| | |
|---|---|
| Vardenafil | 1.00 g |
| Lidocaine | 2.00 g |
| Methanesulphonic acid[1]) | 1.0661–1.1152 g |

-continued

| | |
|---|---|
| Glycerol anhydrous | 1.00 g |
| Purified water | ad 100 ml |

[1] ad pH 3.7

100 µl of this solution were introduced together with an excess of 25% into single-dose nasal spray applicators, closed and heat sterilized at a temperature of 121° C. for 15 minutes. After actuation of the applicator in each case 100 µl of solution (corresponding to 1 mg of vardenafil) are delivered as aerosol.

Example 5

A solution was prepared from the following ingredients:

| | |
|---|---|
| Vardenafil | 2.00 g |
| Polidocanol | 0.10 g |
| Glycerol anhydrous | 2.00 g |
| Methanesulphonic acid | 0.492–0.590 g |
| Purified water | 96.428—96.33 g |
| | 101.02 g |

The solution was filtered through a 0.2 µm filter and introduced together with an excess of 30% into 50 µl single-dose nasal spray applicators, closed and heat sterilized at a temperature of 121° C. for 15 minutes. After actuation of the applicator in each case 50 µl of solution (corresponding to 1 mg of vardenafil) are delivered as aerosol.

Biological tests

Test 1: Comparative pharmacokinetics in dogs

200 µl portions of the solutions from Example 1 and Comparative Example 1 (corresponding to 3 mg of the cGMP PDE inhibitor employed) were administered nasally to female dogs. The pharmacokinetic results of these investigations are indicated in Table 1 below:

TABLE 1

| | Formulation of Example 1 | Formulation of Comparative Example 1 |
|---|---|---|
| $AUC_{stand}$ [kg*h/l] | 0.381 | 0.440 |
| $C_{max,\ stand}$ [kg/l] | 0.204 | 0.263 |
| $t_{max}$ [h] | 0.191 | 0.132 |

The meanings here are:
AUC: Area under the plasma concentration/time plot from time t = 0 to t = infinity
$AUC_{stand}$: AUC divided by the dose administered (mg per kg of body weight)
$C_{max,\ stand}$: Maximum active ingredient concentration in the plasma divided by the dose administered (mg per kg of body weight)
$t_{max}$: Time to reach the maximum active ingredient concentration The results from Table 1 show that the addition according to the invention of a local anaesthetic does not lead to disadvantages in the pharmacokinetics of the composition. There is no excessive peak plasma concentration which might lead to enhanced side effects. In addition, there is no undesirably fast uptake of active ingredient through the addition, according to the invention, of a local anaesthetic either.

Test 2: Comparative tolerability test on healthy subjects 19 healthy subjects each received in a double-blind procedure 100 µl of the solution of Example 3 and 100 µl of the solution of Comparative Example 2 on two different days of the study. The local tolerability of the two solutions was established on the basis of a questionnaire, and the results in Table 2 were obtained.

TABLE 2

Nasal tolerability of vardenafil solutions (10 min. after administration)

| | Example 3 | Comparative Example 2 |
|---|---|---|
| Itching in the nose | | |
| none | 14 | 8 |
| slight | 5 | 6 |
| moderate | | 4 |
| severe | | 1 |
| Watering eyes | | |
| no | 13 | 2 |
| mild | 5 | 9 |
| moderate | 1 | 5 |
| severe | | 3 |
| Nasal airway resistance | | |
| no impairment | 9 | 5 |
| slight impairment | 8 | 9 |
| great impairment | 2 | 5 |
| Stinging in the nose | | |
| none | 14 | 8 |
| slight | 5 | 6 |
| moderate | | 4 |
| severe | | 1 |

(number of subjects in each case)

What is claimed is:

1. A composition comprising at least one cGMP PDE inhibitor and at least one local anaesthetic, with the proviso that the local anaesthetic is not benzyl alcohol, where the cGMP PDE inhibitor is a compound of the formula (I)

$$\text{(I)}$$

in which $R^1$ represents hydrogen or straight-chain or branched alkyl having up to 4 carbon atoms, $R^2$ represents straight-chain alkyl having up to 4 carbon atoms, $R^3$ and $R^4$ are identical or different and represent a straight-chain or branched alkyl chain having up to 5 carbon atoms, which is optionally substituted up to twice, identically or differently, by hydroxyl or methoxy, or $R^3$ and $R^4$ form, together with the nitrogen atom, a piperidinyl, morpholinyl, thiomorpholinyl ring or a radical of the formula

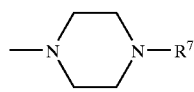

in which
R⁷ denotes hydrogen, formyl, straight-chain or branched acyl or alkoxycarbonyl having in each case up to 6 carbon atoms, or denotes straight-chain or branched alkyl having up to 6 carbon atoms which is optionally substituted once to twice, identically or differently, by hydroxyl, carboxyl, straight-chain or branched alkoxy or alkoxycarbonyl having in each case up to 6 carbon atoms, or denotes $C_{3-8}$-cycloalkyl, and the heterocycles mentioned under R³ and R⁴, which are formed together with the nitrogen atom, are optionally substituted once to twice, identically or differently, optionally also geminally, by hydroxyl, formyl, carboxyl, straight-chain or branched acyl or alkoxycarbonyl having in each case up to 6 carbon atoms, and/or the heterocycles mentioned under R³ and R⁴, which are formed together with the nitrogen atom, are optionally substituted by straight-chain or branched alkyl having up to 6 carbon atoms, which is optionally substituted once to twice, identically or differently, by hydroxyl or carboxyl, and/or the heterocycles mentioned under R³ and R⁴, which are formed together with the nitrogen atom, are optionally substituted by N-linked piperidinyl or pyrrolidinyl, R⁵ and R⁶ are identical or different and represent hydrogen, straight-chain or branched alkyl having up to 6 carbon atoms, hydroxyl or represent straight-chain or branched alkoxy having up to 6 carbon atoms, and salts, isomers and/or hydrates thereof.

2. The composition according to claim 1, comprising 2-{2-ethoxy-5-[(4-ethylpiperazin-1-yl)sulphonyl]phenyl}-5-methyl-7-propylimidazo[5,1-f][1,2,4]triazin-4(3H)-one or a salt, isomer and/or hydrate thereof as cGMP PDE inhibitor.

3. The composition according to either of claims 1 or 2, in which the local anaesthetic is selected from compounds of the formula (II)

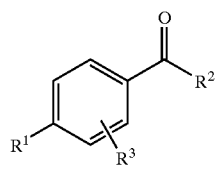

(II)

in which
R¹ represents H, NH₂, NH($C_{1-6}$-alkyl), O—$C_{1-6}$-alkyl or CH₂OPh;
R² represents O—$C_{1-6}$-alkyl which may optionally have a radical from the group consisting of NH($C_{1-6}$-alkyl), N($C_{1-6}$-alkyl)₂ or a saturated 5- or six-membered heterocycle which contains at least one nitrogen atom and is linked via the latter, and optionally one or two further heteroatoms from the group consisting of N, O, S, and optionally carries one to three further $C_{1-6}$-alkyl radicals, or represents (CH₂)$_{1-6}$-Het, where Het represents a saturated 5- or six-membered heterocycle which contains at least one nitrogen atom and is linked via the latter, and optionally one or two further heteroatoms from the group consisting of N, O, S, and optionally carries one to three further $C_{1-6}$-alkyl radicals;

R³ represents H, halogen or O—$C_{1-6}$-alkyl;
or compounds of the formula (III)

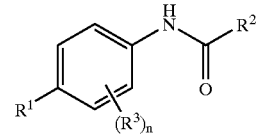

(III)

in which
R¹ represents H or OH;
R² represents $C_{1-6}$-alkyl-N($C_{1-6}$-alkyl)₂ where the bridging alkyl chain may optionally carry one or more $C_{1-6}$-alkyl radicals, or represents a saturated 5- or six-membered heterocycle which contains at least one nitrogen atom and optionally one or two further heteroatoms from the group consisting of N, O, S, and optionally carries one to three further $C_{1-6}$-alkyl radicals,
R³ represents $C_{1-6}$-alkyl, halogen or COO$C_{1-6}$-alkyl; and
n represents 1 or 2;
or a compound from the group consisting of

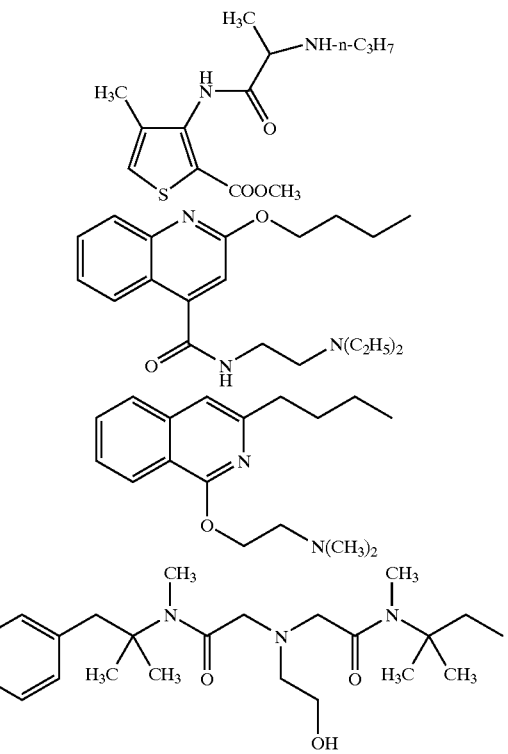

and polidocanol and benoxinate, and physiologically acceptable salts and hydrates thereof.

4. The composition according to claim 3, in which the local anaesthetic is selected from compounds of the formula (II)
in which
R¹ represents H, NH₂, NH-n-C₄H₉, O-n-C₃H₇, O-n-C₄H₉ or CH₂OPh;
R² represents OC₂H₅, O-n-C₄H₉, O—(CH₂)₂N(C₂H₅)₂, O(CH₂)₂N(CH₃)₂, or a radical from the group consisting of

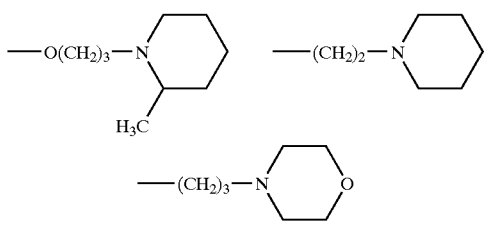

R³ represents H, Cl, O-n-C₃H₇ or O-n-C₄H₉;
or compounds of the formula (III)
in which
R¹ represents H or OH;
R² represents $CH_2N(C_2H_5)_2$, $CHCH_3NH-n-C_3H_7$, $CH_2NH-n-C_4H_9$ or a radical from the group consisting of

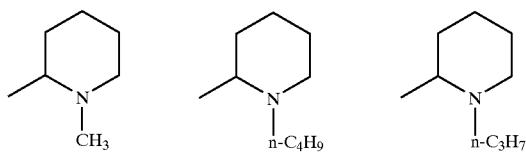

R³ represents CH₃, Cl or COOCH₃;
n represents 1 or 2;
and benoxinate and physiologically acceptable salts and hydrates thereof.

5. The composition according to claim 3, in which the local anaesthetic is selected from benzocaine, butambene, piperocaine, piperocaine hydrochloride, procaine, procaine hydrochloride, chloroprocaine, chloroprocaine hydrochloride, oxybuprocaine, oxybuprocaine hydrochloride, proxymetacaine, proxymetacaine hydrochloride, tetracaine, tetracaine hydrochloride, nirvanin, lidocaine, lidocaine hydrochloride, prilocaine, prilocaine hydrochloride, mepivacaine, mepivacaine hydrochloride, bupivacaine, bupivacaine hydrochloride, ropivacaine, ropivacaine, hydrochloride, etidocaine, etidocaine hydrochloride, butanilicaine, butanilicaine hydrochloride, articaine, articaine hydrochloride, cinchocaine, cinchocaine hydrochloride, oxetacaine, oxetacaine hydrochloride, propipocaine, propipocaine hydrochloride, dyclonine, dyclonine hydrochloride, pramocaine, pramocaine hydrochloride, fomocaine, fomocaine hydrochloride, quinisocaine, quinisocaine hydrochloride, benoxinate and polidocanol.

6. The composition according to claim 3, in which the local anaesthetic is selected from the group consisting of benzocaine, lidocaine, tetracaine, benoxinate, polidocanol and their pharmaceutically acceptable salts.

7. The composition according to claim 3, where the local anaesthetic is lidocaine hydrochloride or lidocaine methanesulphonate.

8. The composition according to claim 1, where the local anaesthetic is present in a concentration of less than 4% (m/v).

9. The composition according to claim 8, where the local anaesthetic is present in a concentration of less than 3% (m/v).

10. The composition according to claim 1, where the cGMP PDE inhibitor is present in an amount of from 0.5 g/kg to 200 g/kg.

11. The composition according to claim 1, additionally comprising solvents and one or more excipients from the group consisting of buffers or substances to adjust the pH, viscosity-increasing substances, preservatives, surfactants, solubilizers, tonicity agents, antioxidants, flavourings, substances to prolong the contact time and humectants.

12. The composition according to claim 11, further comprising one or more carriers.

13. A nasal spray applicator comprising a composition according to claim 1.

14. A nasal spray applicator according to claim 13, which is a single-dose nasal spray applicator.

15. A powder insufflator comprising a composition according to claim 1.

16. A powder insufflator according to claim 3, which is a single-dose powder insufflator.

17. A method for treating diseases comprising administering to a mammal an effective amount of a composition according to claim 1.

18. The method of claim 13 wherein the disease to be treated is male erectile dysfunction.

19. The method of claim 13, wherein the treatment takes place by nasal administration.

20. The composition according to claim 3, where the local anaesthetic is present in a concentration of less than 4% (m/v).

21. The composition according to claim 20, where the local anaesthetic is present in a concentration of less than 3% (m/v).

22. The composition according to claim 3, where the cGMP PDE inhibitior is present in an amount of from 0.5 g/kg to 200 g/kg.

23. The composition according to claim 3, additionally comprising solvent and one or more excipients from the group consisting of buffers or substances to adjust the pH, viscosity-increasing substances, preservatives, surfactants, solubilizers, tonicity agents, antioxidants, flavourings, substances to prolong the contact time and humectants.

24. The composition according to claim 23, further comprising one or more carriers.

25. A nasal spray applicator comprising a composition according to claim 3.

26. A nasal applicator according to claim 25, which is a single-dose nasal spray applicator.

27. A powder insufflator comprising a composition according to claim 3.

28. A powder insufflator according to claim 27, which is a single-dose power insufflator.

29. A method for treating diseases comprising administering to a mammal an effective amount of a composition according to claim 3.

30. The method of claim 29, wherein the disease to be treated is male erectile dysfunction.

31. The method of claim 30, wherein the treatment takes place by nasal administration.

* * * * *